(12) United States Patent
Duenas Carrera et al.

(10) Patent No.: US 8,691,234 B2
(45) Date of Patent: Apr. 8, 2014

(54) VACCINE FORMULATION POTENTIATED BY THE COMBINATION OF DNA AND AN ANTIGEN

(75) Inventors: Santiago Duenas Carrera, Ciudad de la Habana (CU); Juan Morales Grillo, Ciudad de la Habana (CU); Liz Alvarez-Lajonchere Ponce de Leon, Ciudad de la Habana (CU); Alexis Musacchio Lasa, Mariel la Habana (CU); Rolando Pajon Feyt, Bauta la Habana (CU); Ariel Vina Rodriguez, Ciudad de la Habana (CU); Julio C. Alvarez Obregon, Ciudad de la Habana (CU); Nelson Acosta Rivero, Ciudad de la Habana (CU); Gillian Martinez Donato, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 319 days.

(21) Appl. No.: 12/430,534

(22) Filed: Apr. 27, 2009

(65) Prior Publication Data

US 2010/0316669 A1    Dec. 16, 2010

Related U.S. Application Data

(63) Continuation of application No. 10/484,112, filed as application No. PCT/CU02/00005 on Jul. 12, 2002, now abandoned.

(30) Foreign Application Priority Data

Jul. 16, 2001   (CU) .................................. 2001-0171

(51) Int. Cl.
*A61K 39/00*   (2006.01)
(52) U.S. Cl.
USPC .................. 424/184.1; 424/201.1; 424/202.1; 424/203.1; 424/204.1; 424/278.1
(58) Field of Classification Search
None
See application file for complete search history.

(56) References Cited

U.S. PATENT DOCUMENTS

| 6,538,123 B2* | 3/2003 | Barban ........................ 536/23.4 |
| 6,689,757 B1* | 2/2004 | Craig ........................... 514/44 R |
| 7,070,790 B1* | 7/2006 | Bukh et al. .................. 424/228.1 |
| 2002/0002272 A1* | 1/2002 | Houghton et al. .......... 530/388.3 |

FOREIGN PATENT DOCUMENTS

| WO | WO 98/25960 | * | 6/1998 | ............. C07K 14/18 |
| WO | WO 98/50556 | * | 11/1998 | |
| WO | WO 99/30733 | * | 6/1999 | |

OTHER PUBLICATIONS

Rollier et al. Control of Heterologous Hepatitis C Virus Infection in Chimpanzees is Associated with the Quality of Vaccine-Induced Peripheral T-Helper Immune Response. J Virol. 2004, 78(1): 187-196.*
Berzofsky et al. Progress on new vaccine strategies against chronic viral infections. J Clin Invest. Aug. 2004;114(4):450-62.*
Tan et al. Strategies for hepatitis C therapeutic intervention: now and next. Curr Opin in Pharmacology, 2004, 4: 465-470.*
LeRoux-Roels, Development of prophylatic and therapeutic vaccines against hepatitis C virus, Expert Review of Vaccines, vol. 4, No. 3, pp. 351-371 (Jun. 2005).*
Liang et al. Pathogenesis, Natural History, Treatment, and Prevention of Hepatitis C. Ann Intern Med, 2000, 132: 296-305.*
Krastev. The "return" of hepatitis B. World J Gastroenterol 2006; 12(44): 7081-7086.*
The Dictionary of Immunology, Herbert et al. Academic Press, fourth edition, 1995 defining term "vaccine".*
Fournillier et al. Expression of Noncovalent Hepatitis C Virus Envelope E1-E2 Complexes is not Required for the Induction of Antibodies with Neutralizing Properties following DNA Immunization. Journal of Virology, Sep. 1999, p. 7497-7504, vol. 73, No. 9.*

* cited by examiner

*Primary Examiner* — Michelle S Horning
(74) *Attorney, Agent, or Firm* — Hoffmann & Baron LLP

(57) ABSTRACT

Formulation of vaccine antigens, containing as main components: a—) one or several DNA expressing one or several proteins in the immunized individuals and b—) a viral antigen, in appropriate proportions. Development of new formulations, minimizing the number of components that enhance and diversify the spectrum of immune response against different pathogenic entities and generating combined vaccines against pathogens.

Figure 1:
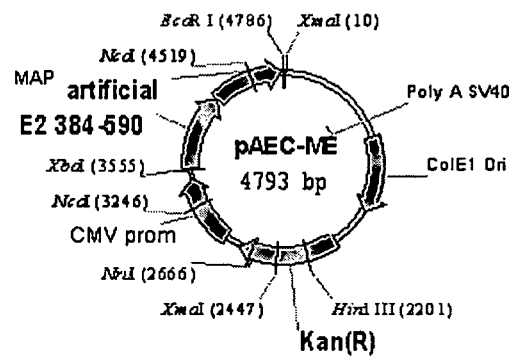
Figure 1:
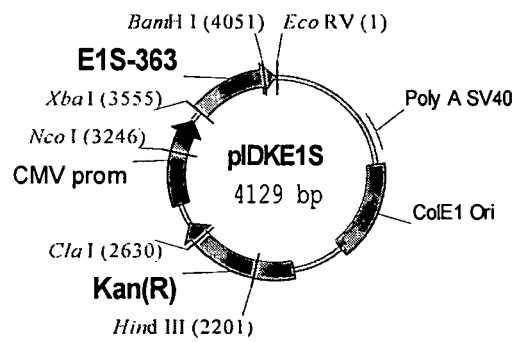
Figure 1:
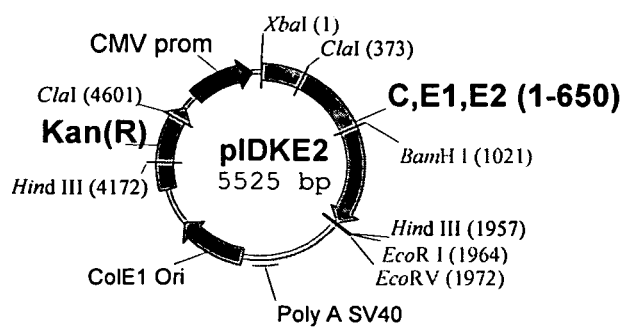

These formulations can be applied in the pharmaceutical industry for preventive and-or therapeutic use in human.

6 Claims, 5 Drawing Sheets

A

B

A

B

Groups
1- pIDKCo-HBsAg
2- pIDKE1S-HBsAg
3- pAEC-ME-HBsAg
4- pIDKE2-HBsAg
5- pIDKE1Sm-HBsAg
6- pAEC-d2-HBsAg-HBsAg
7- pAEC-K6-HBsAg
8- HBsAg-AlOH
9- HBsAg

VACCINE FORMULATION POTENTIATED BY THE COMBINATION OF DNA AND AN ANTIGEN

The present application is a continuation of application Ser. No. 10/484,112 filed on Jun. 3, 2004, now abandoned, which is a U.S. National Phase Application of International Application No. PCT/CU02/00005 filed on Jul. 12, 2002, which asserts priority to Cuban Application No. CU 2001-0171 filed on Jul. 16, 2001. The foregoing applications are hereby incorporated by reference in their entirety herein.

FIELD OF THE INVENTION

The present invention is related with the branch of the medicine, particularly with a new formulation of vaccine antigens. The technical objective of the present invention is the development of new vaccine formulations, minimizing the number of components that are able to induce an enhanced and diverse immune response through the interaction among them. Additionally, the development of combined vaccine formulations is approached in order to increase the immune response induced against the co-administered antigens.

INCORPORATION OF SEQUENCE LISTING

Incorporated herein by reference in its entirety is the Sequence Listing for the application. The Sequence Listing is disclosed on a computer-readable ASCII file titled, "sequence.txt", created on Jan. 5, 2004. The sequence.txt file is 8 kilobytes in size.

BACKGROUND OF THE INVENTION

Several obstacles exist for the obtaining of an effective vaccine against the HCV. Because its RNA nature, HCV can quickly mutate in adaptation to the environment. This contributes to the high diversity of sequences of the multiple viral isolates identified in the world. The biggest heterogeneity concentrates on the hypervariable region I of the HCV E2 protein, where a possible neutralizing epitope has been described. The HCV causes persistent infection in spite of the existence of an active immune response (Lechmann et al., Semin Liver Dis 2000, 20, 211-226). Neither an animal model, nor an in vitro culture system for the efficient replication of the virus and the study about the occurrence of neutralizing antibodies exist. The immunologic patterns associated with the progression of the illness or with the protection have not been defined. It is probable that potent, multispecific and long-lasting both, humoral and cellular immune responses are required for the resolution of the infection (Lechmann et al., Semin Liver Dis 2000, 20, 211-226).

Several approaches have been used to develop a vaccine against the HCV. Recombinant proteins, synthetic peptides, virus like particles, DNA vaccines and live-viral vectors are the most widely evaluated.

The development of a vaccine based on protein subunits was one of the first strategies evaluated for the HCV because for several flaviviruses, antibodies directed against surface proteins can confer protection. Some variants based on the HCV structural antigens have achieved limited protection against the virus in animal models. Such it is the case of the chimpanzees immunized with E1-E2 heterodimers. Seven chimpanzees were vaccinated, five were protected and two developed a self-limiting disease (Choo et al., PROC NATL ACAD SCI USES 1994, 91, 1294-1298). This protection has been correlated with the presence of antibodies (Abs) able to inhibit the E2 binding to human cells (Rosa et al., PROC NATL ACAD SCI USES 1996, 93, 1759-1763).

The recombinant E1 protein from an isolate of the genotype 1 b was purified as homodimers self-associating in particles of 9 nm diameter, approximately (Maertens et al., Records Gastroenterol Belg 2000, 63, 203). Two chimpanzees chronically infected with HCV received 9 doses of 50 µg of the recombinant E1 protein. The vaccination improved the hepatic histology and determined the disappearance of the viral antigens of the liver. Vaccination with recombinant E1 protein also reduced the levels of alanine aminotransferase (ALT). Although the levels of viral RNA in serum didn't change during the treatment, the liver inflammation and the levels of viral antigens increased after treatment. An association was observed between the high levels of antibodies against E1 and the improvement of the illness (Maertens et al., Records Gastroenterol Belg 2000, 63, 203).

Particularly, the formation of virus-like particles from recombinant proteins and their employment as vaccines is very attractive because these structures frequently simulate viral properties. This kind of particles, obtained from insect cells infected with a recombinant baculovirus containing the sequence of the HCV structural antigens, have been able to generate both humoral and cellular immune response against these antigens (Baumert et al., Gastroenterology 1999, 117, 1397-407; Lechmann et al., Hepatology 1999, 30, 423-429). Although the results obtained with vaccines based on protein subunits are encouraging, the immune response induced by these variants is mainly humoral, short-term and isolate-specific.

On the other hand, different recombinant viral vectors have been evaluated in the development of a recombinant vaccine against the HCV. Particularly, recombinant adenoviral vectors are interesting candidates due to their liver tropism, their power to induce both humoral and cellular immunity, and the feasibility for oral or systemic delivery. Adenoviruses containing the DNA encoding sequence for the HCV structural proteins induce an antibody response against each one of these proteins (Makimura et al., Vaccine 1996, 14, 28-36). Moreover, after immunization in mice with recombinant adenoviruses for C and E1, a specific CTL response is detected against these antigens (Bruna-Romero et al., Hepatology 1997, 25, 470-477). Although these results have been encouraging, the recent problems with the use of recombinant adenoviruses in gene therapy have raised doubts about their employment in humans. Other recombinant viruses, like vaccinia, canary-pox and fowl-pox, containing different HCV genes have induced strong CTL and T-helper immune responses in mice (Shirai et al., J Virol 1994, 68, 3334-3342; Large et al., J Immunol 1999, 162, 931-938). However, these recombinant viruses, as well as other variants of alpha virus like the Semliki Forest Virus are also affected by regulatory issues and security concerns related with their application.

The identification of several epitopes for CD4+ and CD8+ T cells in the HCV polyprotein, which could be important in the viral elimination, support the evaluation of synthetic peptides as vaccine candidates against this pathogen. Different peptides, lipidated or not, containing epitopes of C, NS4 and NS5, have induced a strong CTL response in mice (Shirai et al., J Infect Dis 1996, 173, 24-31; Hiranuma et al., J Gene Virol 1999, 80, 187-193; Oseroff et al., Vaccine 1998, 16, 823-833).

Another strategy used to develop a vaccine against the HCV is based in the possibility of generating Abs against linear epitopes. This alternative has been evaluated basically to generate Abs against the HVR-I of the HCV, with some encouraging results in rabbits and chimpanzees (Esumi et al., Arch Virol 1999, 144, 973-980; Shang et al., Virology 1999, 258, 396-405). Quasi-species is the main problem of selecting the HVR-I as the target for a vaccine against the HCV.

The main obstacle for the peptide vaccines is that those peptides without epitopes for helper T cells can be poorly immunogenics. Moreover, the effectiveness of a vaccine is frequently based on the induction of specific immune response against a wide range of different antigens. These limitations are important weaknesses of this strategy.

The DNA immunization is one of the most recent strategies in vaccine development. A DNA vaccine consists on a purified plasmid containing the sequence coding for an antigen of interest, under the control of a functional transcriptional unit in eucariotic cells. After injection of the plasmid in muscle or the skin, the plasmid is taken up by host cells and the antigen is expressed intracellularly. The expression of the encoded antigens in the host cells is one of the major advantages of this methodology because is similar to viral natural infections. The simplicity to manipulate the DNA, together with the DNA stability that makes possible a relatively cheap large-scale production of DNA, is other advantage of DNA vaccination.

The immune response induced with this kind of vaccines can be modulated by co-immunization with molecules or genes coding for co-stimulatory molecules like cytokines. The genetic constructs can be modified, by insertions or deletions of transmembrane domains, signal sequences for secretion, or other types of residues affecting the intracellular trafficking and processing of the antigen.

Particularly, the DNA immunization has been largely studied in the development of vaccines against the HCV. Different expression vectors encoding full-length or truncated variants of the HCV capsid protein have been generated (Lagging et al., J Virol 1995, 69, 5859-5863; Chen et al., Vaccine Res 1995, 4, 135-144). Other constructs also include the HCV 5' non-translated region (Tokushige et al., Hepatology 1996, 24, 14-20). Plasmids expressing fusion variants to the hepatitis B virus (HBV) surface antigen or other envelope antigens of the HBV have been evaluated (Major et al., J VIROL 1995, 69, 5798-5805). Immunization with these plasmids has generally induced positive CTL and lymphocyte proliferative response.

The HCV envelope proteins have also constituted targets of interest for this type of technology. In the case of the HCV E2, the humoral response seems to be mainly directed to the HVR-1 (Lee et al., Mol Cells 1998, 8, 444-451). Immunization with plasmids expressing intracellular or secreted variants of the E1 and E2 proteins has rendered similar immune response (Lee et al., J VIROL 1998, 72, 8430-8436). The inoculation with bicistronic plasmids expressing the GM-CSF and the HCV E1 or E2 proteins increased both humoral and cellular immune response. Recently, the use of bicistronic plasmids expressing the E1 and E2 proteins were generated to investigate the influence of heterodimer formation between these proteins in vivo on the immune response induced after DNA immunization. When heterodimers were formed, the antibody response against HCV E1 and E2 proteins was not obtained. In sharp contrast, high-level antibody titers, directed to both linear and conformational epitopes, were obtained after immunization with plasmids expressing truncated variants of E1 and E2. Therefore, it seems necessary to avoid the heterodimers formation to obtain a strong antibody response when constructs including these antigens are evaluated (Fournillier et al., J VIROL 1999, 73, 497-504).

The non structural proteins have also been evaluated by this technology. Good results were obtained when the region coding for the C-terminal domain of the NS3 protein was included in a vector that allows the simultaneous and independent expression of this domain and the IL-2 (Papa et al., Res Virol 1998, 149, 315-319). The NS4 and NS5 proteins also generate Abs and CTL responses by this immunization strategy (Encke et al., J IMMUNOL 1998, 161, 4917-4923). Recently, the use of a construction coding for GM-CSF and the non structural proteins of the virión (NS3, NS4 and NS5) induced a potent Ab response and a potentiated lymphoproliferative response against each non structural protein (Cho et al., Vaccine 1999, 17, 1136-1144).

In general, the effective expression of different HCV antigens, as well as the generation of anti-HCV Abs in levels ranging from 1:100 to 1:100 000 according to the combination in study, has been reported for different DNA constructs (Inchauspe et al., Vaccine 1997, 15, 853-856). Additionally, the development of specific CTL and lymphocyte proliferative response has been demonstrated (Inchauspe et al., DNA AND CELL BIOLOGY 1997, 16, 185-195). However, efforts are required to improve this methodology in order to generate stronger both humoral and cellular response against different proteins of the HCV. Thus, some variants like liposomes (Gramzinski et al., Mol Medicine 1998, 4, 109-118) and saponin QS-21 (Sasaki et to the., J Virol 1998, 72, 4931-4939) have been evaluated to increase the immune response induced after DNA vaccination. The dendritic cells as biological adjuvants have been also studied in DNA immunization. Dendritic cells (CD) derived of former genetically modified mouse bone marrow to express tumor antigens, by using viral vectors (Specht et al., J Exp Med 1997, 186, 1213-1221; Brossart et al., J Immunol 1997, 158, 3270-3276; Song et al., J Exp Med 1997, 186, 1247-1256), or RNA (Boczkowski et to the., J Exp Med 1996, 184, 465-472), have demonstrated their capacity to promote T cell response specific for tumor antigens, and prophylactic immunity mediated by cells against tumors in mouse.

At the present, the improvement of vectors for DNA immunization, including the insertion of CpG motifs to increase the immune response against the expressed antigens (Hasan et al., J Immunol Meth 1999, 229, 1-22), and the DNA delivery systems is crucial to overcome the limitations of this technology. Due to the challenges that outlines the HCV infection, and to the absence of a clear definition about the immunologic parameters correlating with the protection against this pathogen, it is possible that an effective vaccine against the HCV shall require a multispecific approach stimulating several aspects of the immune response. The solution of this problem is probably in the combination of several vaccination strategies explored until the moment. Particularly, immunization schedules that combine a prime dose with a DNA vaccine and a booster dose with recombinant proteins or viral vectors (Hu et al., Vaccine 1999, 17, 3160-3170; Pancholi et al., J Infect Dis 2000, 182, 18-27) have been evaluated with results that, although positives, require additional investigations to demonstrate if the prime-boost strategies can really induce a protective immunity against the HCV.

Additionally, for the hepatitis B model, a vaccine composition comprising the complex formed by the hepatitis B surface antigen, an antibody specific for this antigen, and a DNA vaccine expressing for this antigen has been evaluated (Wen et al., U.S. Pat. No. 6,221,664, 1998). This formulation allowed the antigen presentation by different means and a quick induction of immune response that resulted superior regarding to the one generated by the individual variants.

SUMMARY OF THE INVENTION

In the present invention, a vaccine formulation comprising as components only a protein antigen and a plasmid expressing one or several proteins, acting at least one of them as adjuvant of the other one, is described. Particularly, the capsid antigen of the hepatitis C or B virus, and a plasmid expressing individual or polyprotein variants of the HCV E1 protein, are evaluated. Contrary to the composition previously described for the hepatitis B model, the presence of antibodies in the formulation is not required to generate the enhancement of the immune response, thus reducing the number of components required. Additionally, the biggest flexibility in the vaccine composition also allows generating simultaneously potent immune responses against different antigens.

DETAILED DESCRIPTION OF THE INVENTION

The present invention provides the composition and methods to immunize an individual in a prophylactic or therapeutic way against the HCV and the HBV, as well as their combination. It is reported for the first time a vaccine formulation having as components: (a) a DNA that expresses a protein variant that includes regions of the E1 antigen of the HCV envelope and (b) a protein antigen of the HCV or HBV, in appropriate proportions. The novelty of the invention is given by the adjuvant effect of at least one component on the immune response generated against the other one. Antigens coded by the genetic constructs and expressed by the host cells, as well as the protein antigen comprising the vaccine the formulation, are interesting targets to generate an immune response against the HCV and the HBV. Thus, the immune response can be directed against a wide spectrum of important antigens.

The vaccine formulation includes a DNA enhancing the immune response generated against a protein antigen mixed with it; being this effect dependent on the expression of one or several proteins coded by the DNA, in the immunized host. The DNA is obtained from a bacterial strain and purified according to traditional procedures (Horn et al., H Gene Ther 1995, 6, 565-573).

The vaccine formulation comprises in preferred embodiments at least one of the following plasmids: pIDKE1S, pIDKE2 and pAEC-ME, whose DNA sequences coding for the protein variants expressed are identified with the number of sequence of 2-4, respectively.

The pIDKE1S plasmid, expressed a protein that comprise the aa from the 176 to the 363 of the HCV E1 (SEQ ID NO. 2). On the other hand, the pIDKE2 plasmid expressed a protein encompassing the first 650 aa of the viral polyprotein (C, E1 and a part of the E2) (SEQ ID NO. 3). The pAEC-ME plasmid expresses a chimeric protein comprising B and T cells epitopes of different HCV antigens (SEQ ID NO. 4). In these plasmids, the coding sequence for the viral antigens was obtained from the cDNA of a HCV cuban isolate (Morales et al., 1998, WO 98/25960). The pAEC-ME, pIDKE1S and pIDKE2 plasmids contain the coding sequence for the HCV antigens inserted into the multiple cloning site of the pAEC-K6 plasmid (Herrera et al., *Biochem Biophys Res Commun.* 2000, 279, 548-551). The plasmids included in the present invention have the regulatory elements able to direct the antigen expression in human cells. These regulatory elements include a transcriptional unit functional in mammals, integrated for example by the human cytomegalovirus promoter and the polyadenilation signal of the simian virus 40. These plasmids also contain a replication origin in bacteria and a selection marker for the resistance to kanamyicin.

The protein component of the formulation can be a soluble viral antigen able to form particles, with a purity superior to 90%. In preferred embodiments, are component of the vaccine formulation the capsid antigens of the HCV and HBV, that enhanced the immune response generated against the proteins expressed by the DNA mixed with them.

The present invention also contemplates the procedure for the mixture of the DNA with the antigen. The mixture is prepared by addition of components, DNA and antigen, dissolved in an appropriate buffer. In preferred embodiments, the formulation can be prepared by the combination of both components, dissolved in saline phosphate, in 10/1 (w/w) proportion. The mixture is incubated at least 2 h between 26° C. and 30° C., with shaking, before administration to the individuals. This formulation can be administered by intramuscular, subcutaneous, intraperitoneal, intramucosal, intravenous sublingual way, or others. The immunization can be performed by means of syringes, gene gun, sprays or other delivery devices. Each individual receives a dose ranging from 0.001 to 10 mg of each component in a volume determined by the animal species and the immunization method employed.

In the case of vaccine formulations having as components a DNA mixed with a protein antigen, a superior product can be obtained compared with each one of the individual components due to:

It is possible to generate a stronger and diverse both humoral and cellular immune response directed to a broader range of epitopes.

The toxic effect generated by the injection of the adjuvant can be eliminated because the antigen 2 is simultaneously the adjuvant.

It is possible the employment of these formulations as core for combined vaccines.

The process of vaccine formulation doesn't require of adsorption of the antigen.

In the case of the formulations containing a DNA that expressed a protein variant that include regions of the HCV E1 protein, and the HCV capsid protein, a superior product can be obtained compared with each one of the individual components due to:

It is possible to generate a stronger and diverse both humoral and cellular immune response directed to a broader range of epitopes.

The toxic effect generated by the injection of the adjuvant can be eliminated because the antigen 2 is simultaneously the adjuvant.

It is possible the employment of the DNA plus the capsid as core for combined or multivalent vaccines.

On the other hand, the immunization with a DNA that expresses a protein variant that includes regions of the HCV E1 protein increased the immunogenicity of HBV protein antigens, present in the formulation. Particularly, the mixture with the HBsAg or the HBcAg, allows superior results to those obtained with this antigens due to:

a) The levels of IgG induced against the HBsAg are superior to those obtained with the inoculation of the HBsAg with aluminum hydroxide.

b) Constitutes a potential combined vaccine HBV-HCV.

c) The formulation process doesn't require of adsorption of the antigen.

DESCRIPTION OF THE FIGURES

FIG. 1: Schematic representation of the plasmids pAEC-ME, pIDKE1S and pIDKE2.

FIG. 2: Electron microscopy of the particles of the hepatitis C virus capsid (A), of the hepatitis B virus surface antigen (B) and of the hepatitis B virus capsid (C).

FIG. 3A: Immunization schedule with the pIDKE2 plasmid and the Core protein. The animals were immunized intramuscularly with 50 μg of DNA and 5 μg of protein. Graph shows reciprocal mean antibody titer against the HCV structural antigens.

FIG. 3B: Immunization schedule with the pIDKE2 plasmid and the Core protein. The animals were immunized intramuscularly with 50 μg of DNA and 5 μg of protein. Graph shows stimulation index against the HCV structural antigens.

FIG. 4A: Immunization schedule with different plasmids and the protein HBcAg. The animals were immunized intramuscularly with 50 μg of DNA and 5 μg of protein. Graph shows reciprocal mean antibody titer against the HBV capsid.

FIG. 4B: Immunization schedule with different plasmids and the protein HBcAg. The animals were immunized intramuscularly with 50 μg of DNA and 5 μg of protein. Graph shows reciprocal mean antibody titer against the structural antigens of HCV.

Figure 5:
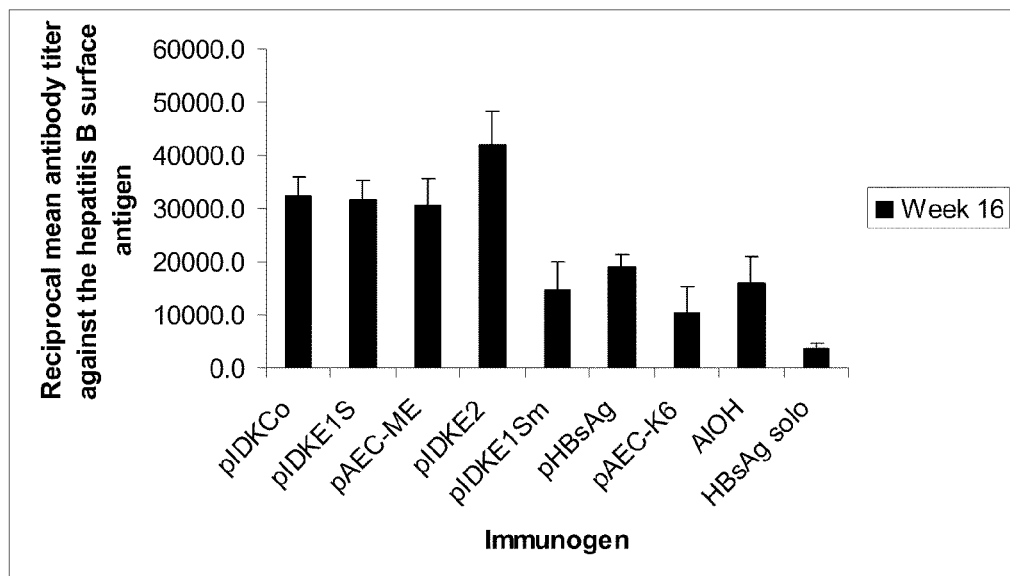

FIG. 5: Immunization schedule with different plasmids and the protein HBsAg. The animals were immunized intramuscularly with 50 μg of DNA and 5 μg of protein.

EXAMPLES

Example 1

Immunogenicity of Formulations Having as Components a DNA that Expresses a Polyprotein Capsid-E1-E2 of the HCV, and the Protein Antigen of the HCV Capsid With the objective of demonstrating the enhancement of the immune response generated against the HCV structural antigens after the administration of the mixture of the plasmid pIDKE2 (FIG. 1), with recombinant HCV capsid particles (FIG. 2A), 10 BALB/c females mice, 8 weeks old, per group were inoculated intramuscularly. The schedule included 2 inoculations in the days 0 and 21, except one of the groups in which the influence of a single dose in day 0 was studied. Blood samples were taken 14 weeks after the first immunization. Immunogens were administered in phosphate buffer saline (PBS). The group 1 was inoculated with 50 μg of the pIDKE2 plasmid (FIG. 1, the plasmid contains the sequence coding for the first 650 aa of the viral polyprotein, SEQ ID NO: 3). The group 2 was inoculated with 5 μg of the Core protein (comprising the first 173 aa of the HCV capsid protein). The group 3 received a first dose with 5 μg of the Core protein and a second one with 50 μg of the pIDKE2 (Core/pIDKE2). The group 4 was inoculated under similar conditions to the group 3 but in inverse order (pIDKE2/Core). The group 5 was inoculated with the mixture of 50 μg of the pIDKE2 and 5 μg of the Core protein in the days 0 and 21 (Core-pIDKE2). The group 6 was inoculated in the same way that the group 5 but only in the day 0 (Core-pIDKE2 (1)). Additionally, a seventh group, negative control, was immunized with 50 μg of the plasmid pAEC-K6 (it doesn't contain sequences coding for the HCV antigens).

The antibody response was determined by ELISA to detect the Ab response against the HCV structural proteins. The Student T test was employed to analyze the results, statistical differences were considered for p<0.05.

Figure 3:
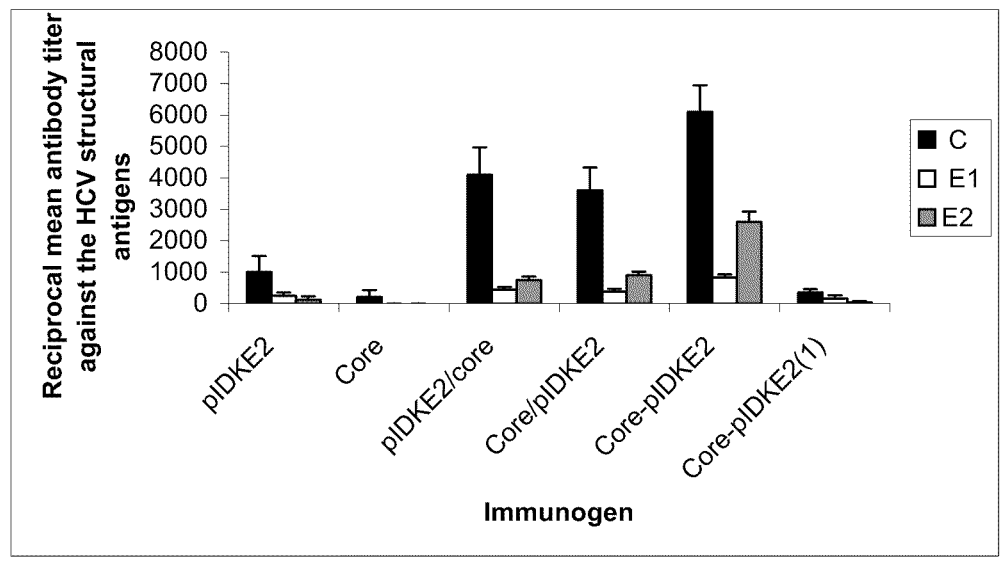
Figure 3:
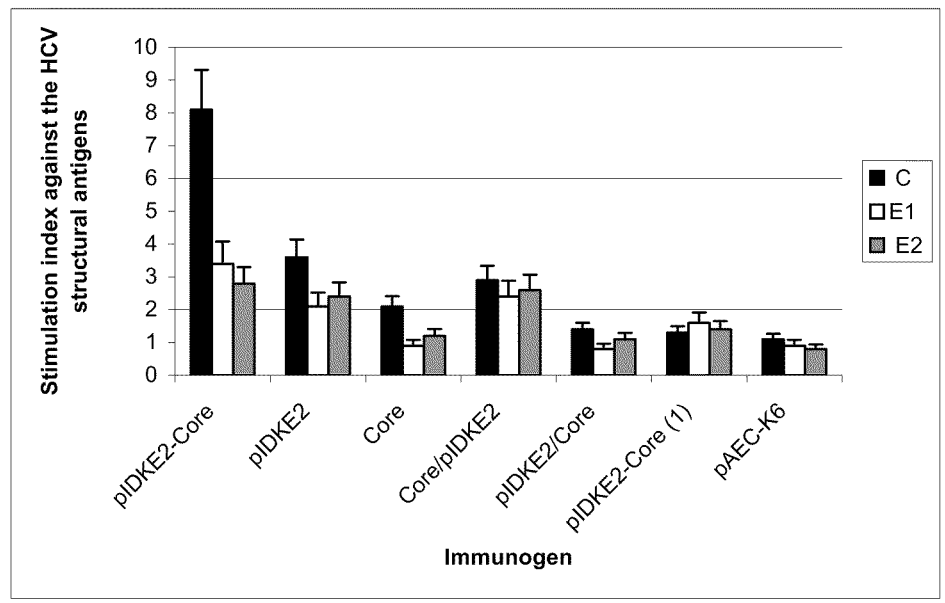

The FIG. 3 shows that it is possible to increase the immune response against the HCV structural antigens by the administration of two doses of the mixture of the pIDKE2 with the Core protein with respect to the individual components. This formulation (in two doses) induced Ab titers against the HCV E1 and E2 envelope proteins statistically higher to those obtained in the remaining groups (FIG. 3A). These Ab titers were also statistically higher to the levels of Abs against the HCV capsid protein, generated by the pIDKE2-Core mixture administered in a single dose (FIG. 3A). The inoculation of the mixture in a single dose always induced the lower levels of Abs among the immunized groups.

The evaluation of the lymphoproliferative response against the HCV structural antigens (FIG. 3B) indicated a significantly superior response against the capsid in the group of animals immunized with the pIDKE2-core in 2 doses, with respect to the remaining groups. The results are shown as the stimulation index of spleen cells obtained from immunized animals. The stimulation index was determined by the ($H^3$) Thymidine uptake. It is possible to conclude that the immunization with the mixture of pIDKE2 and the Core protein generates a synergic stimulation of the immune response induced against the HCV structural antigens.

Example 2

Figure 2:
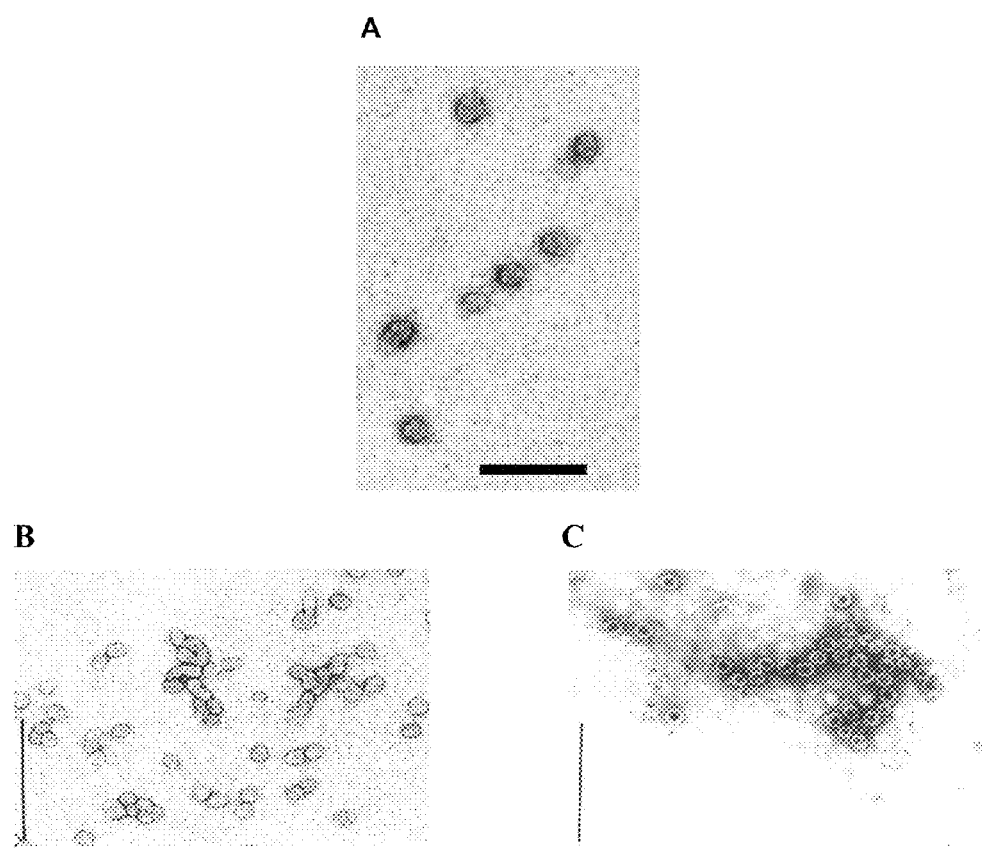

Immunogenicity of Formulations Having as Components a DNA that Expresses a Polyprotein Capsid-E1-E2 of the HCV, and the Protein Antigen of the HBV Capsid With the objective of investigating the behavior of the immune response generated by the mixture of the pIDKE2 plasmid with protein antigens of other pathogens, 10 females BALB/c mice, 8 weeks old, per group were inoculated intramuscularly with the mixture of the above referred plasmid with recombinant particles of the HBV capsid (HBcAg, FIG. 2C). The schedule included 2 inoculations in the days 0 and 21. Blood samples were taken at 9 and 19 weeks after the first immunization. Immunogens were prepared in phosphate buffer saline (PBS). The plasmids were administered in dose of 50 μg, and the HBV capsid protein in dose of 5 μg. The group 1 was inoculated with the plasmid pAEC-K6 (negative control). The group 2 was administered with the HBcAg protein. The group 3 was vaccinated with pIDKE2. The groups 4 and 5 were vaccinated with the mixture of the HBcAg with the plasmids pIDKE2 and pAEC-K6, respectively. The Student T test was employed to analyze the results statistically, a significant difference was considered for p<0.05.

Figure 4:
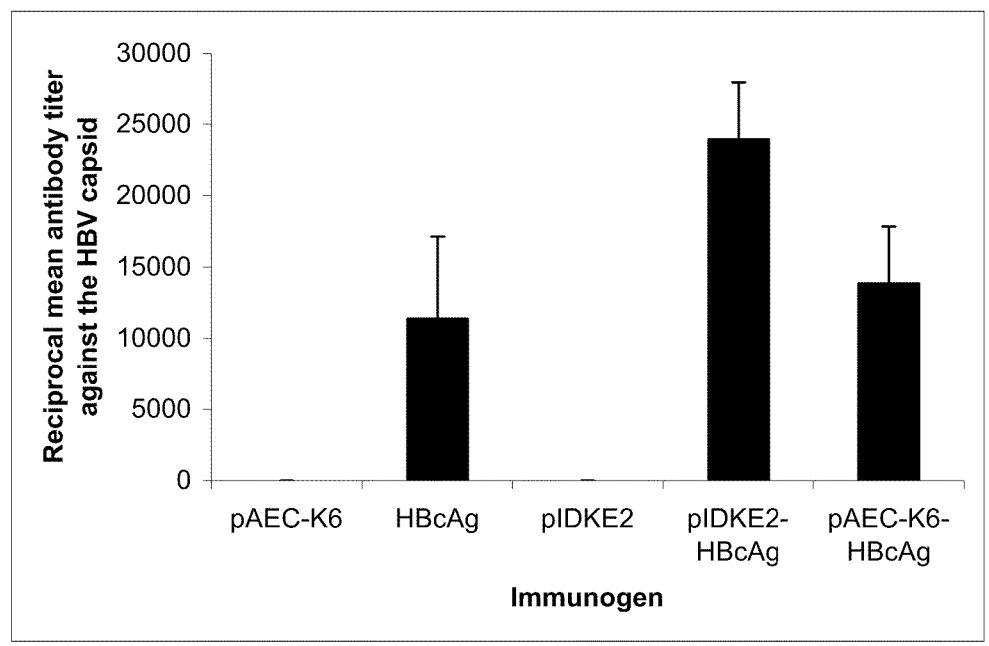
Figure 4:
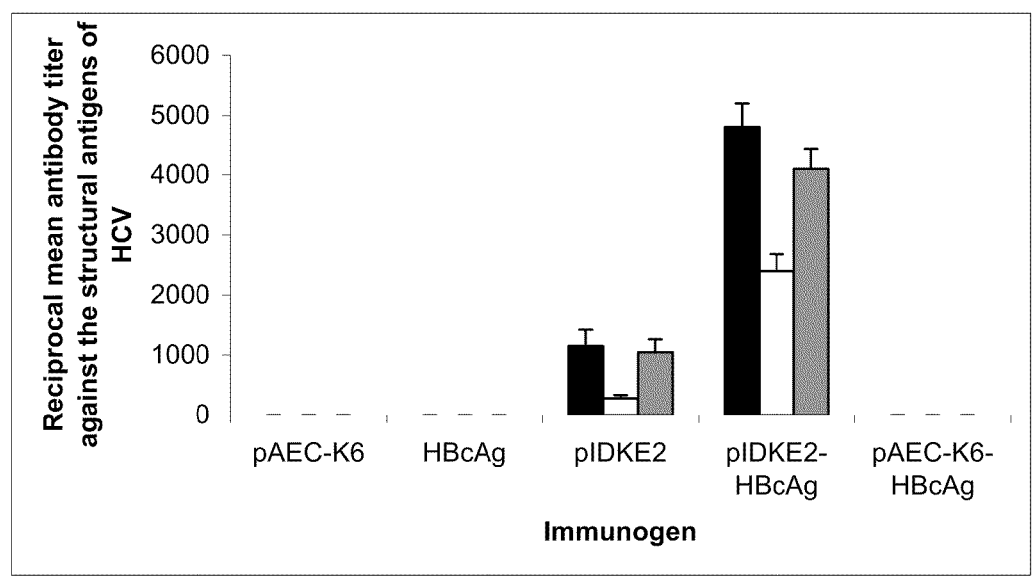

The FIG. 4 shows the antibody response induced in mice 19 weeks after primary immunization. FIG. 4A shows that the mixture of the pIDKE2 plasmid with the HBcAg induced Ab titers against the HBcAg, statistically higher to the observed in the rest of the vaccinated animals. No statistical differences were detected between the groups immunized with HBcAg alone or mixed with the pAEC-K6. Therefore it is possible to conclude that the plasmid pIDKE2 enhance the immune response against the HBcAg.

On the other hand, the FIG. 4B shows that the mixture of the pIDKE2 plasmid with the HBcAg induces antibody titers against the HCV structural antigens higher to those generated in the animals immunized with the pIDKE2 alone. Therefore, the HBcAg is also capable of enhance the immune response induced against the HCV structural antigens induced after the administration of the pIDKE2.

Example 3

Immunogenicity of Formulations Having as Components Plasmids Expressing Variants of the HCV and HBV, and the Protein Variant of the HBV Surface Antigen With the objective of demonstrating the enhancement of the immune response generated against other protein antigens observed after the co-administration with the pIDKE2 plasmid, and to study other plasmids with similar adjuvant properties, 10 female BALB/c mice, 8 weeks old, per group were inoculated intramuscularly with the mixture of the plasmid with recombinant particles of the HBsAg (FIG. 2B). The schedule included 3 inoculations in days 0, 21 and 50. Blood samples were taken at week 16, after the primary immunization. All the immunogens were prepared in phosphate buffer saline (PBS), except a group formulated with Aluminum hydroxide. The group 1 was inoculated with the mixture of 50 μg of the plasmid pIDKCo, containing the sequence coding for the first 176 aa of the HCV capsid protein (Dueñas-Carrera et al., Vaccine 2000; 19(7):992-997), and 5 μg of the HBsAg (pIDKCo-HBsAg). The groups 2 to 7 were inoculated with mixtures of DNA and HBsAg in same quantities but using the following plasmids: group 2 (pIDKE1S-HBsAg), the plasmid pIDKE1S (FIG. 1, containing the sequence coding for the aa 176-363 of the HCV polyprotein, SEQ ID NO. 2); group 3 (pAEC-ME-HBsAg), the plasmid pAEC-ME (FIG. 1, containing the sequence coding for a protein that includes different epitopes of the HCV antigens, SEQ ID NO. 4); group 4 (pIDKE2-HBsAg), the plasmid pIDKE2 (FIG. 1) containing the sequence coding for the aa 1-650 of the HCV polyprotein, SEQ ID NO. 3; group 5 (pIDKE1Sm-HBsAg), the plasmid pIDKE1Sm is identical to the pIDKE1S except that it includes 2 nucleotide insertions in the region coding for the HCV E1 that changes the open reading frame and impedes the expression of this protein (SEQ ID NO. 5); group 6 (pAEC-d2-HBsAg-HBsAg), the plasmid pAEC-d2-HBsAg contains the sequence coding for the HBV HBsAg (Musacchio et al., Biochem Bioph Res Commun 2001, 282, 442-446); group 7 (pAEC-K6-HBsAg), the plasmid pAEC-K6 (negative control, doesn't contain coding sequence under the control of the transcriptional unit). Finally, the groups 8 and 9 were inoculated with 5 μg of HBsAg formulated in Aluminum hydroxide or alone, respectively.

The Student T test was employed to analyze the results statistically, a significant difference was considered for $p<0.05$.

The FIG. 5 shows the Abs titers generated against the HBsAg, 16 weeks after primary immunization. The levels of Abs induced by the HBsAg alone in PBS were statistically inferior to the rest of the variants evaluated except for the mixture formed by the HBsAg and the pAEC-K6. On the other hand, the mixtures of HBsAg with the plasmids pIDKCo, pIDKE1S, pAEC-ME and pIDKE2 induced Ab titres against the HBsAg statistically higher to those induced by the immunization with the HBsAg formulated in Aluminum hydroxide or mixed with the pAEC-K6. The immunization with the HBsAg formulated with aluminum hydroxide or mixed with pAEC-K6, pIDKE1Sm and pAEC-d2-HBsAg induced similar levels of Ab titers against the HBsAg. It is possible to conclude that the expression in the host cells of protein variants that include the amino acid regions of the HCV E1 antigen, from the plasmids administered, enhance the immune response generated against the protein antigen mixed with the DNA construct.

The invention claimed is:

1. An immunogenic composition having as components, i.) a DNA that consists of SEQ ID NO:3 and regulatory elements able to direct expression in human cells, and expresses a protein encoded by SEQ ID NO: 3 in human cells; and ii.) a viral protein antigen consisting of HCcAg, wherein at least one of the components of this composition acts as an adjuvant of the other one.

2. An immunogenic composition according to claim 1, wherein the composition induces an immunogenic response against the hepatitis C virus.

3. A method for inducing an immunogenic response in an individual, the method comprising administering an immunogenic composition to said individual wherein the composition has components i.) a plasmid DNA that consists of SEQ ID NO:3 and regulatory elements able to direct expression in human cells, and expresses a protein encoded by SEQ ID NO: 3; and ii) a viral protein antigen consisting of HCcAg, wherein at least one of the components acts as an adjuvant of the other component.

4. The method according to claim 3, wherein the composition induces an immunogenic response against the hepatitis C virus.

5. A method for enhancing an immune response of components of an immunogenic composition, the method comprising adding i.) a plasmid DNA that consists of SEQ ID NO:3 and regulatory elements able to direct expression in human cells, and expresses a protein encoded by SEQ ID NO: 3; to ii) a viral protein antigen consisting of HCcAg, wherein at least one of the components acts as an adjuvant of the other component, and administering the composition to a patient.

6. The method according to claim 5, wherein the composition induces an immunogenic response against the hepatitis C virus.

* * * * *

SEQUENCE LISTING

```
<160> NUMBER OF SEQ ID NOS: 5

<210> SEQ ID NO 1
<211> LENGTH: 531
<212> TYPE: DNA
<213> ORGANISM: Artificial sequence
<220> FEATURE:
<221> NAME/KEY: misc_feature
<222> LOCATION: (1)..(528)
<223> OTHER INFORMATION: Includes the sequence coding for aa 1 to 176 of
      the HCV core protein
<220> FEATURE:
<223> OTHER INFORMATION: Description of the artificial sequence: pIDKCo
      plasmid

<400> SEQUENCE: 1
atgagcacga atcctaaacc tcaaagaaaa accaaacgta acaccaaccg ccgcccacag        60
gacgtcaagt tcccgggcgg tggtcagatc gttggtggag tttacctgtt gccgcgcagg       120
ggccccaggt tgggtgtgcg cgcaactagg aagacttccg agcggtcgca acctcgtgga       180
aggcgacaac ctatccccaa ggctcgccgg cccgagggca ggtcctgggc ccagcccggg       240
tacccttggc ccctctatgg taacgagggc atgggatggg caggatggct cctgtcaccc       300
cgtggctctc ggcctagttg gggcccccact gacccccggc gtaggtcgcg taatttgggt       360
aaggtcatcg atacccctcac atgcggcttc gccgacctca tggggtacat tccgctcgtc       420
ggcgcccccc taggggggcgc tgccagggcc ctggcgcatg gcgtccgggt tctggaggac       480
ggcgtgaatt atgcaacagg gaatctgccc ggttgctctt tctctctcta a                531

<210> SEQ ID NO 2
<211> LENGTH: 567
<212> TYPE: DNA
<213> ORGANISM: Artificial sequence
```

```
<220> FEATURE:
<221> NAME/KEY: misc_feature
<222> LOCATION: (1)..(564)
<223> OTHER INFORMATION: Includes the nucleotide sequence coding for the
      aa 176-363 on HCV polyprotein, mainly corresponding to the E1
      protein.
<220> FEATURE:
<223> OTHER INFORMATION: Description of the Artificial sequence: pIDKE1S
      plasmid

<400> SEQUENCE: 2
atgttccttt tggctttgct gtcctgtttg accatcccag tttccgccta tgaagtgcgc    60
aacgcgtccg gggtgtacca tgtcacgaac gactgctcca actcaagcat tgtgtatgag   120
gcagacgaca tgatcatgca cccccccgga tgcgtgccct gcgttcggga ggacaacacc   180
tcccgctgct gggtagcgct caccccccaca ctcgcggcca ggaatgccag cgtccccacc   240
acgacaatac gacgccacgt cgatttgctc gttgggggcgg ctgctctctg ctccgctatg   300
tacgtggggg atctctgcgg atctgttttc ctcgtttccc agctgttcac cttctcgcct   360
cgccggcatg agacagcaca ggactgcaac tgctcaatct atcccggcca cgtatcaggt   420
caccgcatgg cctgggatat gatgatgaac tggtcacctt caacagccct agtggtatcg   480
cagttactcc ggatcccaca agccgtcgtg gacatggtag cgggggccca ctggggagtc   540
ctagcgggcc ttgcctacta ctcctaa                                       567

<210> SEQ ID NO 3
<211> LENGTH: 1953
<212> TYPE: DNA
<213> ORGANISM: Artificial sequence
<220> FEATURE:
<221> NAME/KEY: misc_feature
<222> LOCATION: (1)..(1950)
<223> OTHER INFORMATION: Includes the nucleotide sequence coding for aa
      1-650 on HCV polyprotein, encompassing the capsid, E1 and a
      portion of the E2 protein.
<220> FEATURE:
<223> OTHER INFORMATION: Description of the artificial sequence: pIDKE2
      plasmid

<400> SEQUENCE: 3
atgagcacga atcctaaacc tcaaagaaaa accaaacgta acaccaaccg ccgcccacag    60
gacgtcaagt tcccgggcgg tggtcagatc gttggtggag tttacctgtt gccgcgcagg   120
ggccccaggt tgggtgtgcg cgcaactagg aagacttccg agcggtcgca acctcgtgga   180
aggcgacaac ctatcccaa ggctcgccgg cccgagggca ggtcctgggc cagcccggg     240 taccccttggc ccctctatgg taacgagggc atgggatggg caggatggct cctgtcaccc   300
cgtggctctc ggcctagttg gggccccact gaccccggc gtaggtcgcg taatttgggt   360
aaggtcatcg ataccctcac atgcggcttc gccgacctca tggggtacat tccgctcgtc   420
ggcgcccccc tagggggcgc tgccaggggc ctggcgcatg gcgtccgggt tctggaggac   480
ggcgtgaatt atgcaacagg gaatctgccc ggttgctctt ctctctcttt ccttttggct   540
ttgctgtcct gtttgaccat cccagttttcc gcctatgaag tgcgcaacgc gtccggggtg   600
taccatgtca cgaacgactg ctccaactca agcattgtgt atgaggcaga cgacatgatc   660
atgcacaccc ccgatgcgt gccctgcgtt cggaggaca cacctcccg ctgctgggta     720 gcgctcaccc ccacactcgc ggccaggaat gccagcgtcc ccaccacgac aatacgacgc   780
cacgtcgatt tgctcgttgg ggcggctgct ctctgctccg ctatgtacgt gggggatctc   840
tgcggatctg ttttcctcgt ttcccagctg ttcaccttct cgcctcgccg gcatgagaca   900
gcacaggact gcaactgctc aatctatccc ggccacgtat caggtcaccg catggcctgg   960
```

-continued

| | |
|---|---|
| gatatgatga tgaactggtc accttcaaca gccctagtgg tatcgcagtt actccggatc | 1020 |
| ccacaagccg tcgtggacat ggtagcgggg gcccactggg gagtcctagc gggccttgcc | 1080 |
| tactactcca tggtggggaa ctgggccaag gttttgattg tgatgctact ctttgccggc | 1140 |
| gttgacggga cgggaaccta cgtgacaggg gggacggcag cccgcggcgt cagccagttt | 1200 |
| acgggcctct ttacatctgg gccgagtcag aaaatccagc ttgtaaatac aacggcagc | 1260 |
| tggcatatta accggactgc cctgaactgc aacgactccc tccagaccgg gttccttgct | 1320 |
| gcgttgtttt acgtgcacag gttcaactcg tccggatgct cagatcgcat ggccagctgc | 1380 |
| cgccccattg atacgttcga ccaggggtgg ggccccatta cttacgctga gccgcgcagc | 1440 |
| ttggaccaga ggccctattg ctggcactac gcacctcaac cgtgtggtat cgtacccgcg | 1500 |
| gcggaggtgt gtggtccagt gtattgtttc actccaagcc ccgttgtcgt ggggaccacc | 1560 |
| gatcgttccg gcgtccctac gtataactgg ggggagaatg agacggacgt gctgctcctt | 1620 |
| aacaacacgc ggccgccgct gggcaactgg tttggctgta catggatgaa tagcactggg | 1680 |
| ttcaccaaga cgtgcggggg ccctccgtat aacatcggag gggtcggtaa caacaccttg | 1740 |
| acctgcccta cggattgctt ccgcaagcac cccgaggcca cttacaccaa atgtggtttg | 1800 |
| gggccttggt tgacacctag gtgcttggtc gactacccat acaggctttg gcattacccc | 1860 |
| tgcactgtca actttaccat cttcaaggtt cggatgtatg tgggggcgt ggagcacagg | 1920 |
| cttaccgctg catgcaactg gactcgagga taa | 1953 |

<210> SEQ ID NO 4
<211> LENGTH: 1194
<212> TYPE: DNA
<213> ORGANISM: Artificial sequence
<220> FEATURE:
<221> NAME/KEY: misc_feature
<222> LOCATION: (1)..(1191)
<223> OTHER INFORMATION: Includes the nucleotide sequence coding for different epitopes of HCV proteins.
<220> FEATURE:
<223> OTHER INFORMATION: Description of the Artificial sequence: pAEC-ME plasmid

<400> SEQUENCE: 4

| | |
|---|---|
| atgacgggaa cctacgtgac agggggacg gcagcccgcg gcgtcagcca gtttacgggc | 60 |
| ctctttacat ctgggccgag tcagaaaatc cagcttgtaa ataccaacgg cagctggcat | 120 |
| attaaccgga ctgccctgaa ctgcaacgac tccctccaga ccgggttcct tgctgcgttg | 180 |
| ttttacgtgc acaggttcaa ctcgtccgga tgctcagatc gcatggccag ctgccgcccc | 240 |
| attgatacgt tcgaccaggg gtggggcccc attacttacg ctgagccgcg cagcttggac | 300 |
| cagaggccct attgctggca ctacgcacct caaccgtgtg gtatcgtacc cgcggcggag | 360 |
| gtgtgtggtc cagtgtattg tttcactcca gccccgttg tcgtggggac caccgatcgt | 420 |
| tccggcgtcc ctacgtataa ctgggggag aatgagacgg acgtgctgct ccttaacaac | 480 |
| acgcggccgc cgctgggcaa ctggtttggc tgtacatgga tgaatagcac tgggttcacc | 540 |
| aagacgtgcg ggggccctcc gtataacatc ggaggggtcg gtaacaacac cttgacctgc | 600 |
| cctacggatt gcttccgcaa gcacggatcc acccacgtga ccggcggcag ccaggcccgc | 660 |
| accacccaca gcttccacct cctgctgcgc cagggcgcca gcagaacgt gcagctgatc | 720 |
| gccgacctga tgggctacat cccactggtg ggcgccccac tgggcaagaa gggccacgtg | 780 |
| agcgccacc gcatggcctg gacatgatg atgaactggg ccagcaagaa ggccgccagc | 840 |
| cgcgccgccg gcttgcagga cagcaccatg ctggtgagcc acccgcgt gaccggcggc | 900 |

-continued

```
gtggccggcc acgtgaccag cggcctggtg tccctgttca gccctggcgc cagccagaag    960
atccagctgg tgggctccag cttcagcctg ttcctgttgg ccctcctgag cagcttgacc   1020
atcaagaaga tgagctactc ctggaccggc gccctggtga ccccaagcgc cgccgagaag   1080
aagctgttgt tcaacatcct gggcggctgg gtgaagaaga gcatggtggg caactgggcc   1140
aaggtgaaga agtacaccgg cgacttcgac agcgtgatcg actccaggcc ttaa         1194

<210> SEQ ID NO 5
<211> LENGTH: 569
<212> TYPE: DNA
<213> ORGANISM: Artificial sequence
<220> FEATURE:
<223> OTHER INFORMATION: Description of the artificial sequence:
      pIDKE1Sm plasmid
<220> FEATURE:
<221> NAME/KEY: misc_feature
<222> LOCATION: (1)..(566)
<223> OTHER INFORMATION: Includes the nucleotide sequence coding for the
      HCV E1 with 2 nucleotides insertions changing the ORF and
      originates a nonrelated small protein.

<400> SEQUENCE: 5
attgttcctt ttggctttgc tgtcctgttt gaccatccca gtttccgcct atgaagtgcg     60
caacgcgtcc ggggtgtacc atgtcacgaa cgactgactc caactcaagc attgtgtatg    120
aggcagacga catgatcatg cacacccccg gatgcgtgcc ctgcgttcgg gaggacaaca    180
cctcccgctg ctgggtagcg ctcacccccca cactcgcggc caggaatgcc agcgtcccca    240
ccacgacaat acgacgccac gtcgatttgc tcgttggggc ggctgctctc tgctccgcta    300
tgtacgtggg ggatctctgc ggatctgttt tcctcgtttc ccagctgttc accttctcgc    360
ctcgccggca tgagacagca caggactgca actgctcaat ctatcccggc cacgtatcag    420
gtcaccgcat ggcctgggat atgatgatga actggtcacc ttcaacagcc ctagtggtat    480
cgcagttact ccggatccca caagccgtcg tggacatggt agcgggggcc cactggggag    540
tcctagcggg ccttgcctac tactcctaa                                      569
```